(12) United States Patent
Feng et al.

(10) Patent No.: US 9,752,913 B2
(45) Date of Patent: Sep. 5, 2017

(54) METHOD FOR DETERMINING THE EMPTY STATE OF AN IV BOTTLE IN AN IV INFUSION MONITORING DEVICE

(71) Applicants: Jun Feng, Lincoln, MA (US); Xueming Miao, Wuxi (CN)

(72) Inventors: Jun Feng, Lincoln, MA (US); Xueming Miao, Wuxi (CN)

(*) Notice: Subject to any disclaimer, the term of this patent is extended or adjusted under 35 U.S.C. 154(b) by 485 days.

(21) Appl. No.: 14/290,941

(22) Filed: May 29, 2014

(65) Prior Publication Data
US 2015/0346013 A1  Dec. 3, 2015

(51) Int. Cl.
  G01F 23/20  (2006.01)
  G06F 17/40  (2006.01)
  G06F 19/00  (2011.01)
  G01F 23/00  (2006.01)
  G01F 1/00  (2006.01)
  A61M 5/14  (2006.01)
  A61M 5/168  (2006.01)

(52) U.S. Cl.
  CPC ....... *G01F 23/0076* (2013.01); *A61M 5/1414* (2013.01); *A61M 5/16845* (2013.01); *A61M 5/16895* (2013.01); *G01F 1/00* (2013.01); *G01F 23/20* (2013.01); *A61M 2205/18* (2013.01); *A61M 2205/50* (2013.01); *A61M 2205/502* (2013.01); *A61M 2205/60* (2013.01); *A61M 2205/6054* (2013.01); *A61M 2205/8206* (2013.01); *G06F 17/40* (2013.01); *G06F 19/00* (2013.01)

(58) Field of Classification Search
None
See application file for complete search history.

(56) References Cited

U.S. PATENT DOCUMENTS

| | | | | |
|---|---|---|---|---|
| 3,055,551 | A * | 9/1962 | Johnson | G07F 9/02 200/81.9 R |
| 3,656,478 | A | 4/1972 | Swersey | |
| 3,939,360 | A | 2/1976 | Jackson | |
| 4,589,372 | A | 5/1986 | Smith | |
| 4,670,007 | A | 6/1987 | Wheeldon | |
| 5,563,584 | A | 10/1996 | Rader | |
| 7,654,668 | B2 * | 2/2010 | Neuhann | A61B 3/113 351/205 |
| 7,694,589 | B2 * | 4/2010 | Mehus | G01G 3/14 177/25.11 |
| 8,728,020 | B2 * | 5/2014 | Caleffi | A61M 1/342 604/5.01 |
| 9,649,422 | B2 * | 5/2017 | Johnson | A61M 1/36 |
| 2005/0137653 | A1 | 6/2005 | Friedman | |
| 2006/0064053 | A1 | 3/2006 | Bollish | |
| 2009/0151474 | A1 * | 6/2009 | Mehus | G01G 3/14 73/862.52 |

(Continued)

*Primary Examiner* — Edward Cosimano

(57) ABSTRACT

A method for determining the empty state of an IV bottle is provided in an IV infusion monitoring device or in a networking monitoring system, which is cable to monitor the infusion data during whole infusion process. The infusion data includes the weight of remaining medical liquid in the IV bottle, the infusion rate and the remaining time from completion as well as the empty state. It also gives alarm as the measured gross weight of the IV bottle drops to the empty state. The empty state is determined preferably in terms of necking effect and needle tip effect, or their combination.

7 Claims, 11 Drawing Sheets

(56) References Cited

U.S. PATENT DOCUMENTS

| | | | |
|---|---|---|---|
| 2009/0212070 A1* | 8/2009 | Johnson | A61M 1/36 222/58 |
| 2010/0147876 A1* | 6/2010 | Mehus | G01G 3/14 222/1 |
| 2010/0280430 A1* | 11/2010 | Caleffi | A61M 1/342 604/5.01 |
| 2012/0285545 A1* | 11/2012 | Johnson | A61M 1/36 137/1 |
| 2013/0233394 A1* | 9/2013 | Nguyen | A61J 1/20 137/2 |

* cited by examiner

SET UP OF AN IV INFUSION MONITORING DEVICE

IV INFUSION MONITORING DEVICE 10

SIGNAL PROCESSOR 21

MICROPROCESSOR 43

FIG. 4
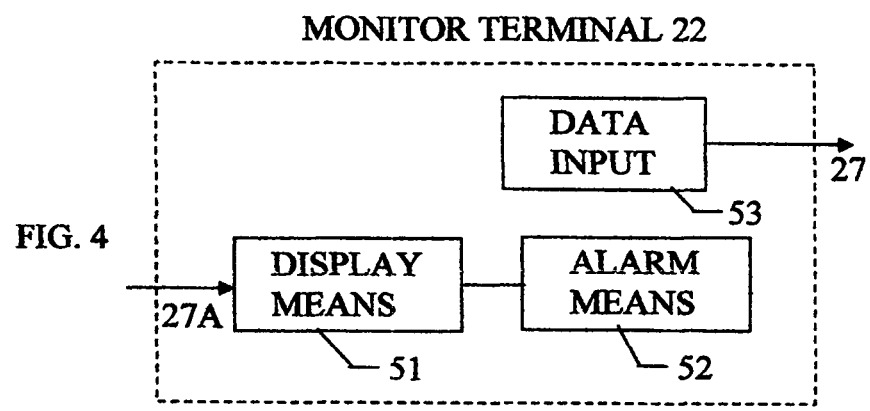
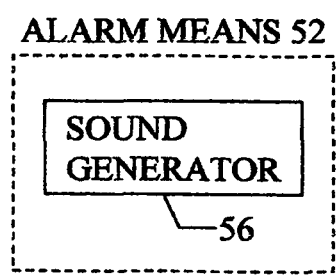
FIG. 4A
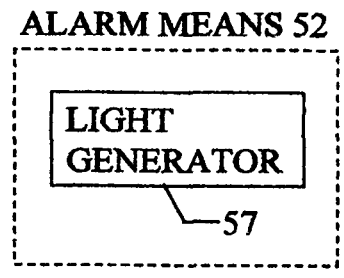
FIG. 4B

METHOD FOR DETERMINING THE EMPTY STATE OF AN IV BOTTLE IN AN IV INFUSION MONITORING DEVICE

CROSS REFERENCE TO RELATED APPLICATIONS

This application is a CIP of application Ser. No. 12/932,128, filed on Feb. 17, 2011, now abandoned as was published as US 2011/0205074 A1, by the present inventors to US Patent and Trademark Office. It is also noted that the above mentioned non-provisional applications claim the benefit of provisional patent application No. 61/338,636, filed on Feb. 22, 2010 by the present inventors to US Patent and Trademark Office.

FEDERALLY SPONSORED RESEARCH

Not applicable

SEQUENCE LIST OF PROGRAM

Not applicable

FIELD OF INVENTION

The present invention relates to a method for determining the empty state of an IV bottle during gravity infusion process in an IV infusion monitoring device or in a network monitoring system, which allows the hospital workers to monitor the infusion process remotely and in mobile way

BACKGROUND OF THE INVENTION

Assume a patient lies on bed to receive 1V infusion. There are two types of infusion systems. One is by pump, another is by gravity. The pump infusion system is very costly and often encounters maintenance trouble. Therefore, many hospital workers prefer to use the traditional gravity infusion system. The gravity IV infusion line consists of three parts: (a) An IV bottle contains medical liquid and air above the medical liquid; (b) Infusion line includes a liquid needle inserted inside the IV bottle to receive medical liquid, a plastic liquid tube with one end connected to the liquid needle as liquid inlet and another end connected to the IV injection needle for injecting the medical liquid into the patient vein. A drop chamber is connected in the middle of the liquid tube for observing the liquid flow rate. A switch is connected also in the middle of the liquid tube to control the flow rate manually; (c) Air line includes an air needle inserted into the IV bottle to apply air pressure for driving the liquid flow, and a plastic air tube with one end connected to the air needle as air outlet and another end opened to the environment as air inlet. It is noted that some hospitals have removed the air line for the above setup if the IV bottle is made of flexible plastic bag. As the medical liquid in the IV bottle drops to an empty state, that is, the IV bottle is almost empty, the IV bottle must be replaced by a new one, otherwise air may enter the infusion line and causes serious medical problems.

So far, the job of bottle replacement needs frequent supervision from patient and nurses by eyeball. This task becomes a heavy burden of medical workers, particularly at night. To develop an alarming system at the empty state for IV infusion becomes a big demand from hospitals and patients. The accurate determination of the empty state becomes very important, if it is determined being too high or too early, a lot of medical liquid may be wasted, if it is determined being too low or too later, the medical liquid in the IV bottle may be completely drained before a nurse replaces a new IV bottle and therefore a medical accident may occur. In addition, the weight of the medical liquid in an IV bottle may vary widely because its different specific density and additive medicines. Also, the weight of an empty IV bottle varies widely because of it different material, size and manufacturer etc. Therefore, estimate of the empty state by using flow rate integration or by estimating the weight of an empty IV bottle may generate a big error.

Furthermore, the hospitals also wish to monitor whole IV infusion process for better care of the patients. For example, an IV infusion process may go wrong if a patient or particularly a baby moves violently during infusion. In this case, monitoring whole infusion process, e.g., the liquid level and the infusion speed at each time moment, becomes necessary. Unfortunately, there is no any satisfied device existing in the current market for this task.

The present invention provides a method for accurately determining the empty state of an IV bottle in an IV infusion monitoring device or in a network monitoring system, which not only gives alarm when the IV bottle needs replacement, but also provides all infusion data during whole infusion process, e.g., the liquid level (remaining liquid weight), the liquid flow rate (infusion rate) and the remaining time from the completion of the infusion process as well as the empty state. The present invention also includes a communication network, so that the nurses or other hospital workers can monitor the whole IV infusion process of each patient from either a close or a remote location through the network.

U.S. Pat. No. 3,656,478 to Swersey, discloses an infusion monitor which is able to supply a medical liquid to a patient at either a high rate or low rate, depending upon the weight of the patient. If the weight of the patient decreases below a preset value, the infusion monitor is switched to the high speed. If the weight of the patient returns to normal, the infusion monitor switches back to the low speed. The present invention is apparently different from the Swersey's. The present invention provides a method for determining the empty state in an IV infusion monitoring device, which can measures and monitors the weight of the medical liquid in the IV bottle, and calculates the liquid flow rate during infusion.

U.S. Pat. No. 3,939,360 to Jackson discloses a liquid level sensor and electrode assembly therefore. Jackson's disclosure applies three capacitance plates to measure the capacitance which is related to the liquid level. The present invention is related to an IV infusion monitoring device, which applies weight measurement of the medical liquid in the IV bottle by an electric load sensor to monitor the infusion process.

U.S. Pat. No. 4,589,372 to Smith discloses a dispensing system similar to the Swersey's. The Smith's system first determines the weight of an animal subject, and then a delivery unit supplies a predetermined amount of material to the animal subject. The amount of supplied material is a function of the weight of the subject. It is apparent that the present invention is completely different from the Smith's. The present invention is related to a device, which monitors the weight of the remaining medical liquid in the IV bottle and the liquid flow rate during infusion, not the control of the infusion speed as a function of the weight of the animal subject.

U.S. Pat. No. 4,670,007 to Wheeldon et al. discloses an infusion monitoring system by measuring the weight loss of the fluid container. Wheeldon's invention is for controlling the infusion rate of a pump-based infusion system, in which the infusion rate is controlled by the pump. Although Wheeldon includes an empty state indicator, it does not disclose any method to set up the empty state. However, the present invention discloses methods for accurately determining the empty state in an infusion monitoring device used to monitor all infusion data including weight, flow rate and time etc.

U.S. Pat. No. 5,563,584 to Rader et al. discloses a liquid level sensing and monitoring system for medical fluid infusion systems. Rader's disclosure applies pressure sensor technology. A pressure sensor is inserted into the outlet of a liquid container and contacts the liquid for detecting the liquid level. The present invention is related to a monitoring device, which applies the load sensor for measuring the weight of the medical liquid in the IV bottle during infusion.

US Pat. Application No. US2005/0137653A1 to Friedman discloses a very general monitoring system for monitoring a plurality of medical devices including infusion pump. However, it does not disclose any communication system to have remote and mobile monitoring function. Furthermore, it does not disclose specifically any method for determining the empty state of an IV bottle for infusion monitoring purpose.

US Pat. Application No. US2006/0064053A1 to Bollish et al. discloses a monitoring system to monitor and control 2 pump devices at same time. The present invention is related to an infusion monitoring device for monitor a gravity-driven infusion system. Furthermore, Bollish does not disclose any method for determining the empty state of the IV bottle.

The present invention provides a method for determining the empty state of an IV bottle in an TV infusion monitoring device or in a network monitoring system, which is capable for measuring and monitoring the infusion data during whole infusion process, as well as for giving alarm when the gross weight of the IV bottle drops to the empty state. The present invention is apparently different from and superior over all the prior arts in function, structure, cost, accuracy and reliability, as well as ease of use.

SUMMARY OF THE INVENTION

A method for determining the empty state of an IV bottle during gravity infusion is provided in an IV infusion monitoring device or in a network monitoring system, which is capable to monitor the infusion data during whole infusion process for gravity-driven infusion system remotely and in mobile way. However, it is not suitable for pump based infusion system. The infusion data includes the weight of remaining medical liquid in the IV bottle, the liquid flow rate (i.e., infusion rate) as number of drop per minute during infusion and the remaining time from the completion of the IV infusion process as well as the empty state etc. It also gives alarm as the medical liquid in the IV bottle drops to the empty state of the IV bottle. The empty state of the IV bottle is defined as the gross weight of an almost empty IV bottle plus its attachment, at which the nurse must replace a new IV bottle in order to have continuous infusion process. The monitoring devices further combines with a server and at least one mobile device to form a communication network for IV infusion monitoring (i.e., network of things or internet of things for IV infusion monitoring). The mobile devices include at least one of a remote desk top computer in a nurse station, a PDA device (personal digital assistant), a laptop computer, a palmtop computer (e.g., ipad), a smart phone (e.g., iphone), a smart watch (e.g. Android smartwatch) and smart glasses (e.g., Google glasses) etc. The infusion data are transmitted from the monitoring device to the server and then to at least one of mobile devices through the communication network by wire or wirelessly. Therefore the nurses and other hospital workers can monitor the IV infusion process in a remote and mobile device as an option, e.g. a desktop computer in a nurse station or a mobile device carried by a nurse or a hospital worker etc. However, as another option, if using network monitoring system, the monitoring device only measures the remaining weight of the medical liquid in the IV bottle as a function of time, which is then transmitted to a server via the network. It is the server that contains software to analyze and calculate the infusion data, which is then transmitted back to the monitoring device and other mobile device for monitoring purpose.

An IV infusion system with gravity as driving force (i.e., gravity-driven infusion system) is used for injecting a medical liquid to a patient vein. It includes an IV bottle containing medical liquid in its lower part and air above the medical liquid. The IV bottle is a liquid container, which is functioned as medical liquid supplier. It can be made of plastic bottle, plastic bag or glass bottle etc. Both a liquid needle for liquid flow and an air needle for air flow are inserted into the bottom of an IV bottle. A plastic liquid tube for liquid flow is connected at the end of the liquid needle. A plastic air tube for air flow is connected at the end of the air needle. A drop chamber is connected in the middle of the liquid needle for observing the liquid flow rate. A switch is connected under the drop chamber for the nurse to control the liquid flow rate. It is noted that some hospitals have removed the air needle and air tube from the IV bottle if the IV bottle is made of a flexible plastic bag, however, for this case, the present invention is still valid. Optionally, an infrared sensor is disposed outside the drop chamber to measure more accurately the liquid flow rate.

The infusion monitor device comprises a load sensor, a signal processor, a monitor terminal and a power. The load sensor measures the gross weight of the IV bottle including the medical liquid and the attachments e.g., the needles and the tubes. The measured weight signal is then transmitted to the signal processor, which is able to process the measured weight signal and obtain the infusion data including the weight of remaining medical liquid in an IV bottle, the liquid flow rate during infusion and the remaining time from the completion of the IV infusion process. The signal processor also compares the measured gross weight to the empty state of the IV bottle, and sends out an alarm signal to the monitor terminal as the measured gross weight is equal or less than the empty state value. Meanwhile, all the infusion data are sent from the signal processor to the monitor terminal for display during infusion process. The power is provided preferably by a battery or a solar cell, alternatively by an external power source as an option to user.

The load sensor includes at least one strain gage. As a mechanical load (i.e., the gross weight of the IV bottle) is applied, the load is sensed by the strain gage, which outputs an electric signal, e.g., a voltage, in proportional to the applied mechanical load. The strain gage can be bonded or un-bonded, can be made of metal or semiconductor, can be made of resistor or capacitor or inductor. To compensate the temperature change and obtain the best resolution, typically, at least one strain gages and other electric parts (e.g., resistor, capacitor and inductor) form an electric bridge circuit consisting of 4 arms and 2 pair of ends, in which two ends receive an applied voltage while another two ends output the electric signal in proportional to the applied load on the at least one strain gage.

The signal processor comprises (a) a signal amplifier, which is able to amplify the measured weight signal (e.g., a voltage) received from the load sensor, (b) an A/D converter, which converts the amplified weight signal (e.g. an analog voltage) into a plurality of digital data, (c) a microprocessor, which has memory to store data as well as has software to analyze the plurality of digital data statistically and obtain the infusion data. There is much interference electrically or mechanically during infusion process, for example, as the patient moves or IV bottle is touched, the measured signal values vary. The microprocessor receives a plurality of digital data during infusion process including interference and noise. The software in the microprocessor is able to statistically analyze these data and filter out the interference and noises in order to obtain accurate weight measurement of the medical liquid as a function of time. The liquid flow rate of the medical liquid in the IV bottle is calculated as weight change per unit time, it can be converted into number of drop per unit time by using the estimated weight of each drop. The software is also capable for evaluating the initial weight of the medical liquid in the IV bottle. In addition, the software compares the measured gross weight of the IV bottle with the empty state value, and sends out an alarm signal as the measured gross weight is equal or less than the empty state value.

The monitor terminal comprises (a) a display mean which is able to display all infusion data including the weight of remaining medical liquid in the IV bottle, liquid flow rate and the time from the completion of the IV process, (b) an alarm means which gives alarm as the monitor terminal receives an alarm signal from the signal processor, and (c) a data input means which receives data input and sends them to the signal processor. The data input means includes manual input or the input from the communication network. The display means includes a liquid-crystal screen on the monitor terminal. The alarm means includes a sound generator or a light generator.

There are two different monitoring modes, one is single monitoring mode, and another is network monitoring mode. In single monitoring mode, the monitoring is carried out in each monitoring device. In network monitoring mode, each set of data including weight and time data, or infusion data is communicated through the communication network by wire or wirelessly between each monitoring device and a remote device, e.g., a desktop computer in a nurse station or a server, a mobile device carried by a nurse in a remote location.

The procedure to monitor the IV infusion process is described as the followings. The load sensor measures the gross weight Wg of the IV bottle including the medical liquid and the attachments, e.g., the needles and the tubes as a function of time. The measured weight signal is transmitted to a signal amplifier for amplification. An A/D converter receives the amplified signal from the signal amplifier and converts the analog signal to a plurality of digital data, which are then passed to a microprocessor for data analysis statistically to filter out all interference and noise etc. The microprocessor then calculates the weight change $\Delta W$ as a function of time during infusion. Since all parts have fixed weight except the medical liquid during infusion, the weight change must be the weight decrease of the medical liquid during infusion. The initial weight Wo of the medical liquid is evaluated at the beginning of the infusion process by one of 3 different methods: (a) Evaluated by the software in microprocessor based the standard weight category of the medical liquid in the IV bottle; (b) Manual input from monitor terminal; (c) Input from the communication network. All the IV data from a doctor is inputted into the computer system including the patient name, IV identification, the name and quantity of the medicine and solution etc. These IV data are stored in the computer system, and will be transmitted into the microprocessor through the communication network. The weight of remaining medical liquid in the IV bottle is calculated based on the difference between the initial weight of the medical liquid in the IV bottle and the weight change during infusion: $Wr=Wo-\Delta W$. The percentage of the remaining medical liquid weight and the liquid flow rate are then respectively: Wr/Wo % and dW/dt. The remaining time from completion of the infusion process is obtained by dividing Wr by dW/dt. These liquid level data are sent to the monitor terminal for display in single monitoring mode, and are also sent to the communication network so that a nurse or a hospital worker can monitor the infusion process from a remote location. The microprocessor also compares the gross weight of the IV bottle to the empty state value, and sends an alarm signal to the monitor terminal to generate an alarm if the gross weight is equal or less than the empty state value. Meanwhile if the liquid flow rate is too low in comparison to a predetermined rate vale due to some accident during the infusion process, an alarm will also be generated to alert the nurses.

The preferred embodiment of the present invention is a methodology for determining the empty state of the IV bottle based on either necking effect or needle tip effect, or their combination in terms of single monitoring system with network addition. It is experimentally observed that, as the medical liquid level drops to near or a little below the tip of the liquid needle, the infusion rate (i.e., liquid flow rate) abruptly reduces. This is called needle tip effect. This methodology based on needle tip effect includes the following 4 steps: (a) the infusion rate is measured continuously; (b) liquid level drops to near or a little below the needle tip; (c) the needle tip effect is observed and then the empty state is determined; (d) the alarm is activated and the empty state is displayed. It is also experimentally observed that, as the medical liquid level drops to the necking area of the IV bottle, the infusion rate (i.e., liquid flow rate) fast and gradually reduces. This is called necking effect. This methodology based on necking effect includes the following 4 steps: (a) the infusion rate is measured continuously; (b) liquid level drops to the necking area; (c) the necking effect is observed and then the empty state is determined; (d) the alarm is activated and the empty state is displayed. It is noted that the above two methodologies can be combined to form a new methodology for determining the empty state of the IV bottle. However, the preferred embodiment also involves data communication through network, which is an addition to the basic single monitoring system.

The alternative embodiment of the present invention is a methodology for determining the empty state of the IV bottle in terms of networking monitoring system with different signal route from the preferred embodiment as the following: the monitoring device, instead of measuring and calculating the infusion data as in the preferred embodiment, only measures the gross weight signal in digital format as a function of time. The digital data of the measured gross weight as a function of time is transmitted wirelessly to the server via the communication network. The server contains software to statistically analyze and calculate the infusion data based on the received weight data as a function of time. The calculated infusion data in the server is then transmitted wirelessly back to the monitoring device and other mobile devices for monitoring. The infusion data includes the weight of remaining medical liquid in the IV bottle, the liquid flow rate (i.e., infusion rate) as number of drop per minute during infusion, the remaining time from the completion of the IV infusion process and the empty state of the IV bottle. The method to determine the empty state of the IV bottle is again based on either necking effect or the needle tip effect, or their combination In summary, the difference between two embodiments is that the infusion data is calculated by the monitoring device itself in the preferred embodiment, but the infusion data is calculated by the server through the network in the alternative embodiment. Apparently, the new signal route design in the alternative embodiment greatly simplifies the monitoring device by fully using the network function. Therefore, the design of the alternative embodiment is in fact a monitoring system integrated by the communication network (networking monitoring system), in comparison, the design of the preferred embodiment is a single monitoring system, which is able to work alone, but with a network addition. The method of determining the empty state for both the embodiments is the same, that is, to based on either necking effect or the needle tip effect, or their combination.

BRIEF DESCRIPTION OF THE DRAWINGS

FIG. 4 is a block diagram of an exemplary monitor terminal in the present invention.

FIG. 4A is a block diagram of an exemplary alarm means of the monitor terminal in the present invention.

FIG. 4B is a block diagram of an alternative alarm means of the monitor terminal in the present invention.

DETAILED DESCRIPTION OF THE ILLUSTRATIVE EMBODIMENTS

Figure 1:
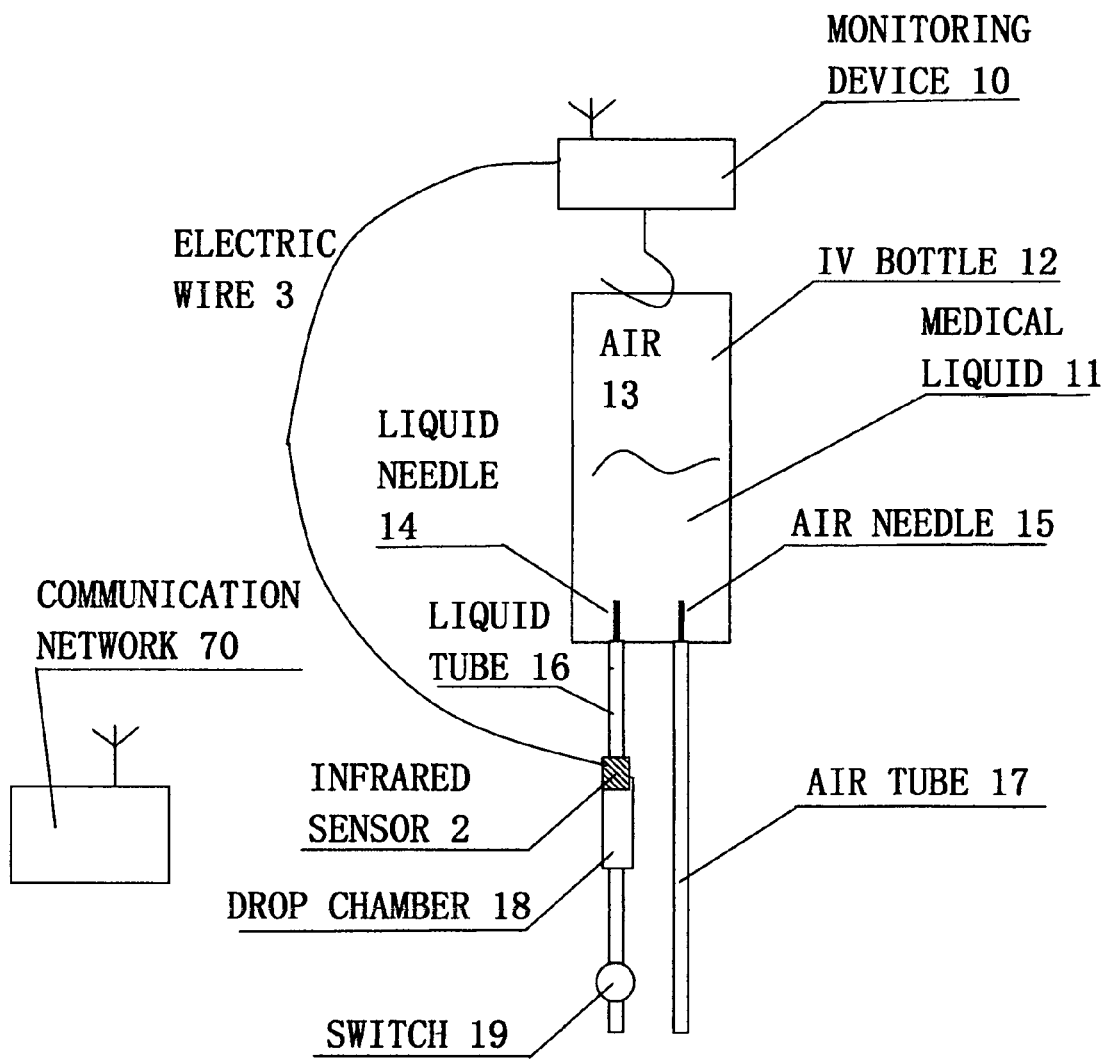
FIG. 1 is a schematic drawing of the setup of an IV infusion monitoring device in the present invention.

In describing preferred embodiment of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

FIG. 1 is a schematic drawing of the setup of an IV infusion monitoring device 10 in the present invention that is capable of monitoring the infusion data during whole infusion process. It is for the gravity-driven infusion system, not for the pump-based infusion system. The infusion data includes the weight of the remaining medical liquid 11 in an IV bottle 12 or the ratio of the weight of the remaining medical liquid 11 over the initial weigh of the medical liquid 11, liquid flow rate (i.e., infusion rate), and the remaining time from completion of IV process. It gives alarm when the weight of the remaining medical liquid 11 in the IV bottle 12 drops to an empty state of the IV bottle 12. It also gives alarm if the IV infusion process encounters some trouble and results in a very slow liquid flow rate below a predetermined rate value. The empty state of the IV bottle 12 is the gross weight of an almost empty IV bottle 12 plus its attachments, at which the medical liquid 11 in the IV bottle 12 is almost finished so that the nurse must replace a new IV bottle 12 for continuous infusion process.

The IV infusion monitoring device 10 is installed in an IV post, which is fixed in a patient bed or seat, or stands alone next the patient bed or seat, or it is installed in an IV bar, which is fixed above the patient bed or seat horizontally. Alternatively, the IV infusion monitoring device 10 can be installed or held in any other position near the patient as long as the IV bottle 12 is relatively stable during infusion as well as it is above the patient to provide enough gravitational driving force for the medical liquid flow.

An IV infusion system comprises the IV bottle 12, a liquid needle 14, an air needle 15, a liquid tube 16 and an air tube 17. The IV bottle 12 contains the medical liquid 11 in its lower part and the air 13 above the medical liquid 11. The IV bottle 12 functions as a liquid supply source during infusion. The IV bottle 12 can be made of stiff materials such as glass or harden plastic bottle, or it can be made of flexible plastic bags. The liquid needle 14 and an air needle 15 are inserted into the bottom of the IV bottle 12. The liquid tube 16 is connected at the end of the liquid needle 14. The air tube 17 is connected at the end of the air needle 15. The medical liquid 11 flows from the IV bottle 12 through the liquid needle 14 and liquid tube 16 into the vein of a patient by gravity force. A drop chamber 18 is connected in the middle of the liquid tube 16 for observing the liquid flow rate or infusion rate (drop per minute). A switch 19 is connected with the liquid tube 16 for manually controlling the liquid flow rate. The weight of the medical liquid 11 can be converted from weight unit (g) to volume unit (ml). The liquid flow rate can be converted from weight per unit time into the number of liquid drop per unit time based on estimated weight per drop. It is noted that some hospitals have removed the air needle 15 and air tube 17 from the IV bottle 12 if the IV bottle 12 is made of a flexible plastic bag, however, for this case, the present invention is still valid.

Furthermore, as an option, a pair of infrared sensors 2 is disposed outside the drop chamber 18 for detecting the liquid flow rate. The measured data are transferred via electric wire 3 to the IV infusion monitoring device 10. The infusion data are communicated, via communication network 70, with a server and at least one mobile devices including at least one of PDA devices, laptop computer, palmtop computer (e.g., ipad), smart phone (e.g., iphone), smart watches (e.g., Android smartwatch, a watch including a CPU and displays) and smart glasses (e.g., Google smartglasses, a pair of glasses containing a CPU and displays) etc. Therefore, it allows the hospital workers and nurses to monitor the infusion process remotely and in mobile manner.

Alternatively, the monitoring device 10 only measures the gross weight signal in digital format as a function of time, the digital data of the measured gross weight as a function of time is transmitted wirelessly, via the communication network 70, to the sever, which contains a software to statistically analyze and calculate the infusion data based on the received weight and time data. The calculated infusion data by the server is then transmitted wirelessly back to the monitoring device 10 and other mobile devices.

Figure 2:
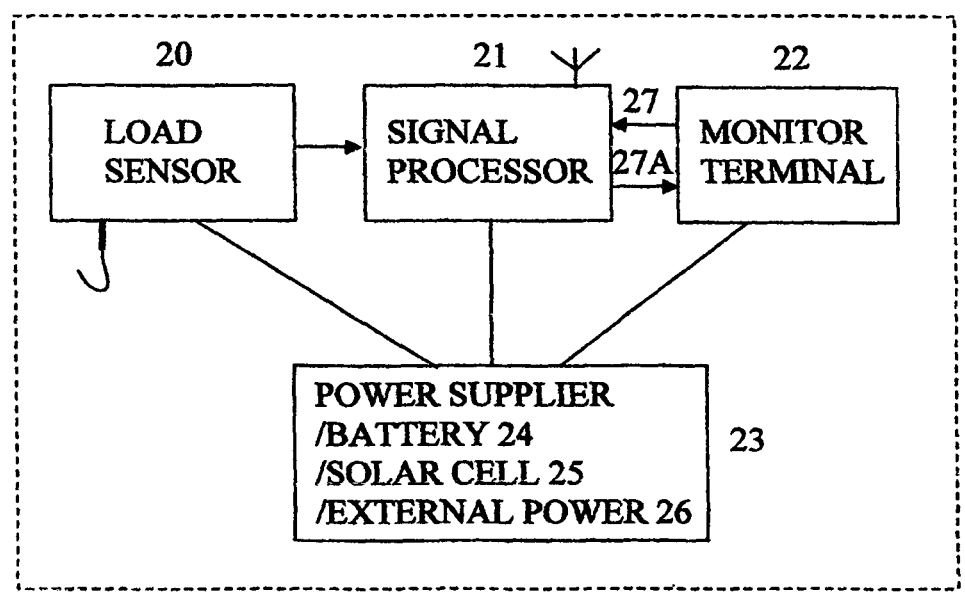
FIG. 2 is a block diagram of an exemplary IV infusion monitoring device in the present invention.

FIG. 2 is a block diagram of an exemplary IV infusion monitoring device 10 in the present invention. The IV infusion monitoring device 10 comprises a load sensor 20, a signal processor 21, a monitor terminal 22 and a power 23. The load sensor 20 measures the gross weight of the IV bottle 12 including the medical liquid 11 and its attachments e.g., the needles 14, 15 and the tubes 16, 17. The measured weight signal is then transmitted to the signal processor 21, which is able to process the signal and to calculate the infusion data including the weight of the remaining medical liquid 11 in the IV bottle 12 or the ratio of the weight of the remaining medical liquid 11 over the initial weigh of the medical liquid 11, liquid flow rate (i.e., infusion rate), and the remaining time from completion of IV process. The signal processor 21 also compares the measured gross weight to the empty state value, and sends out an alarm signal to the monitor terminal 22 as the measured gross weight is equal or less than the empty state value. All the infusion data are sent from the signal processor 21 to the monitor terminal 22 by wire 27A for display during infusion process. The monitor terminal 22 gives an alarm in response to the alarm signal from the signal processor 21. In addition, the monitor terminal 22 is capable of transmitting an input data to the signal processor 21 by wire 27. The power 23 is provided preferably by a battery 24 or a solar cell 25, alternatively by an external power source 26 as an option to user. If the power is provided by a battery 24 or a solar cell 25, the negative pole of the battery 24 or solar cell 25 will act as a reference zero potential point, and therefore, all parts are non-grounded and the monitoring device 10 becomes portable, i.e., it can move around with a patient while in working condition.

Alternatively, the signal processor 21 only processes the gross weight signal in digital format as a function of time, the digital data of the measured gross weight as a function of time is transmitted out wirelessly, via the communication network 70, to the sever, which contains a software to statistically analyze and calculate the infusion data based on the received weight and time data. The calculated infusion data in the server is then transmitted wirelessly back to the monitoring device 10 and other mobile devices for display.

Figure 3:
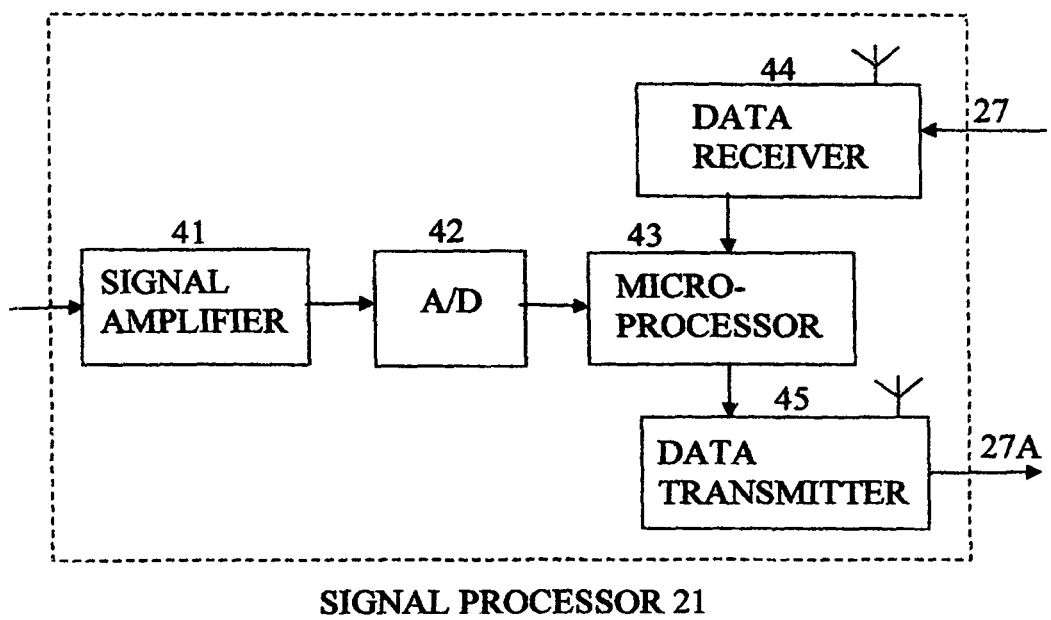
FIG. 3 is a block diagram of an exemplary signal processor in the present invention.
Figure 3A:
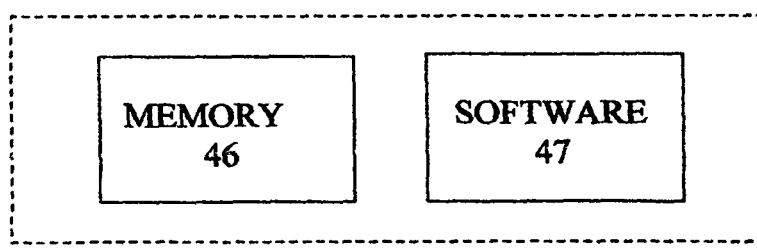
FIG. 3A is a block diagram of an exemplary microprocessor including memory and software in the present invention.
Figure 5:
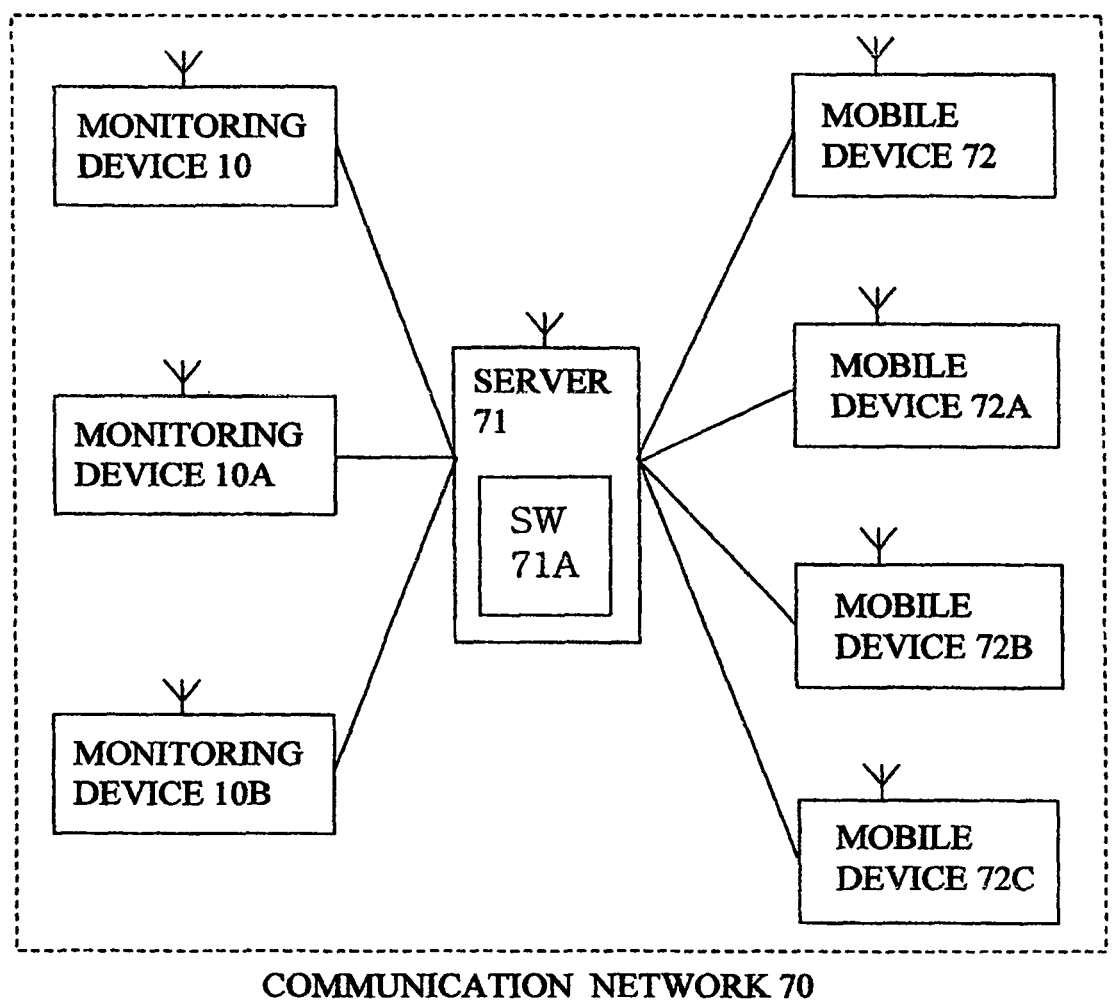
FIG. 5 is a block diagram of a communication network by using the monitoring device.

FIG. 3 is a block diagram of an exemplary signal processor 21 in the present invention. The signal processor 21 comprises a signal amplifier 41, an A/D converter 42, a microprocessor 43, a data receiver 44 and a data transmitter 45. The signal amplifier 41 is able to amplify the measured weight signal (e.g., a voltage) received from the load sensor 20. The A/D converter 42 converts the amplified weight signal (e.g. an analog voltage) into a group of digital data. The microprocessor 43 contains a memory 46 to store data as well as a software 47 (FIG. 3A) to analyze the digital data statistically and to obtain the infusion data. The data receiver 44 receives input data from monitor terminal 22 by wire 27. The data transmitter 45 sends out infusion data to monitor terminal 22 by wire 27A. There is much interference electrically or mechanically during infusion process, for example, as the patient moves or IV bottle 12 is touched, the measured weight signal values vary. The microprocessor 43 receives a plurality of data during infusion process; these data also include interference and noises. The software 47 in the microprocessor 43 is able to statistically analyze these data to filter out the interference and noises in order to obtain accurate weight measurement of the medical liquid 11 in the IV bottle 12 as a function of time. The software 47 is also capable for evaluating the initial weigh of the medical liquid 11 in the IV bottle 12. The initial weight of the medical liquid 11 can also be obtained alternatively from manual input in the monitor terminal 22 or from a communication network 70 (FIG. 5). The liquid weight can be converted from weight unit (g) to volume unit (ml) by using the liquid specific weight. The liquid flow rate is calculated as weight change per unit time. However, the unit of the flow rate can be converted from weight per unit time to number of drops per unit time by using estimated weight per drop. The remaining time from the completion of IV process is obtained based on the remaining liquid weight and the liquid flow rate. In addition, the software 47 compares the measured gross weight or the liquid flow rate to the empty state value or the predetermined rate values, and sends out an alarm signal as the measured weight or liquid flow rate are equal or less than the empty state value or predetermined rate value respectively.

Alternatively, the microprocessor 43 contains a memory 46 to store the gross weight signal in digital format as a function of time, as well as a software 47 (FIG. 3 A) to encode the digital data of the measured gross weight as a function of time. These data are sent to the data transmitter 45, which then transmits them wirelessly, via the communication network 70, to the server. The server contains software to statistically analyze and calculate the infusion data based on the received weight and time data. The calculated infusion data by the server is then transmitted wirelessly back to the monitoring device 10 and other mobile devices for monitoring purpose.

FIG. 4 is a block diagram of an exemplary monitor terminal 22 in the present invention. The monitor terminal 22 comprises a display mean 51, an alarm means 52 and a data input means 53. The display means 51 is able to display the infusion data. The alarm means 52 gives alarm as the monitor terminal 22 receives an alarm signal from the signal processor 21. The data input means 53 receives data input manually or from the communication network 70 (FIG. 5), and sends them to the signal processor 21. The monitor terminal 22 communicates with the signal processor 21 by wire 27, 27A. The display means 51 includes a liquid-crystal screen on the monitor terminal 22. The alarm means 52 includes either a sound generator 56 (FIG. 4A) or a light generator 57 (FIG. 4B).

FIG. 5 is a block diagram of a communication network 70 by using the monitoring device. There are two different monitoring modes, one is single monitoring mode, and another is network monitoring mode. In single monitoring mode, the monitoring device 10 alone is applied for each patient, and the IV infusion process is monitored by using the monitoring device 10 only. In network mode, a communication network 70 (i.e., internet of things or network of things for IV infusion monitoring) comprises at least one monitoring device 10, 10A, 10B, a server 71 and at least one mobile device 72, 72A, 72B, 72C. The mobile devices include at least one of PDA devices, laptop computers, palmtop computers (e.g., ipad), smart phones (e.g., iphone), or smart watch (e.g., Android smartwatch), and smart glasses (e.g., Google swart glasses) etc. Each monitoring device 10, 10A, 10B is located next to each patient under IV infusion process for measuring the infusion data including the liquid level Wr or Wr/Wo %, the liquid flow rate (i.e., the infusion rate) dW/dt and the remaining time tr from the completion of IV process. The server 71, typically a personal computer in nurse station or in other control center, includes display means for displaying received infusion data, as well as software 71A to analyze and to manage data flow within the communication network 70. Each mobile device 72, 72A, 72B, 72C, e.g., a remote desk top computer in the nurse station, a laptop computer, a palmtop computer or a smart pone, smart watch, a pair of smart glasses or other mobile devices, is carried by a nurse or a hospital worker. Each mobile device includes display means for displaying received infusion data, and as an option, a data reader means e.g., a magnetic stripe reader, a barcode scanner or a RFID tag reader for scanning and reading in the IV data contained in the data label attached outside the IV bottle 12. The infusion data are transmitted from at least one monitoring device 10, 10A, 10B to the server 71 by wire or wirelessly. The server 71 further sends all the infusion data to each mobile device 72, 72A, 72B, 72C by wire or wirelessly. In reverse turn, the IV data including patient name, IV identification, the name and quantity of medicine and solution etc. are read by the mobile device 72, 72A, 72B, 72C and they are then transmitted back to server 71 and further to each monitoring device 10, 10A, 10B. The server 71 is also capable to directly receive input data from the users.

Alternatively, the server 71 receives the digital data of the measured gross weight as a function of time from the monitoring device 10-10B wirelessly via the communication network 70. The sever 71 contains software 71A to statistically analyzing and calculate the infusion data based on the received weight data as a function of time. The calculated infusion data by the sever 71 is then transmitted wirelessly back to the monitoring device 10-10B and other mobile devices 72-72C.

Figure 6:
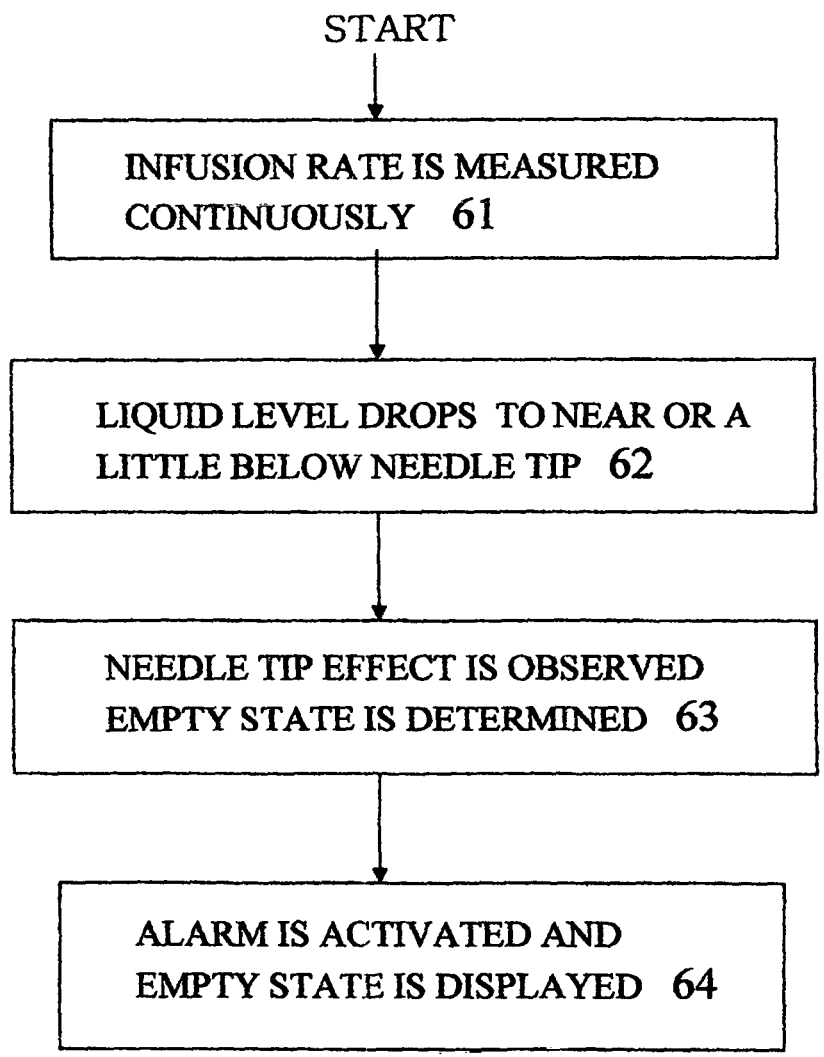
FIG. 6 is the logic flow chart for a methodology based on needle tip effect.

FIG. 6 is a logic flow chart to describe the methodology for determining the empty state of the IV bottle 12 based on needle tip effect in the present invention. It is experimentally observed that, as the medical liquid level drops to near or a little below the tip of the liquid needle 14 (FIGS. 1 and 7), the infusion rate (i.e., liquid flow rate) abruptly reduces. This is called needle tip effect. FIG. 6 describes the following 4 steps for this methodology: (a) the infusion rate is measured continuously (61); (b) liquid level drops to near or a little below the needle tip (62); (c) the needle tip effect is observed and then the empty state is determined (63); (d) the alarm is activated and the empty state is displayed (64).

Figure 6A:
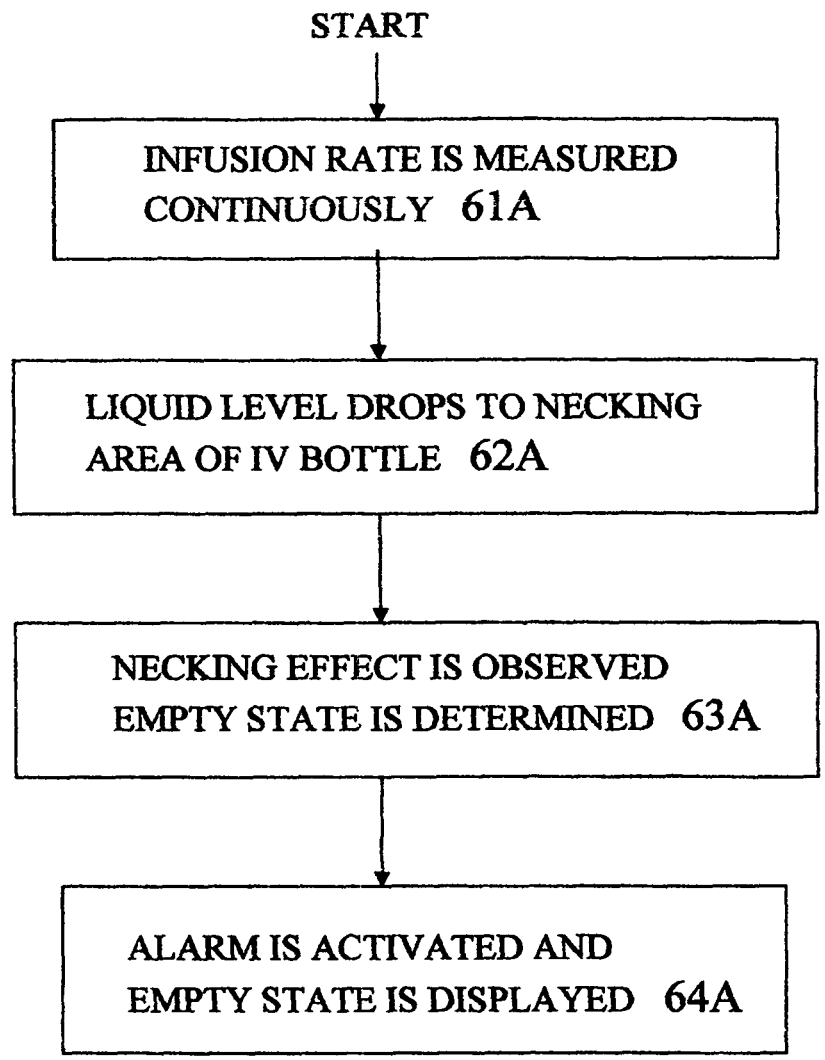
FIG. 6A is the logic flow chart for a methodology based on necking effect.

FIG. 6A is a logic flow chart to describe the methodology for determining the empty state of the IV bottle 12 based on necking effect in the present invention. It is experimentally observed that, as the medical liquid level drops to the necking area of the IV bottle 12 (FIG. 7), the infusion rate (i.e., liquid flow rate) fast and gradually reduces. This is called necking effect. FIG. 6A describes the following 4 steps for this methodology: (a) the infusion rate is measured continuously (61A); (b) liquid level drops to the necking area (62A); (c) the necking effect is observed and then the empty state is determined (63A); (d) the alarm is activated and the empty state is displayed (64A).

Figure 6B:
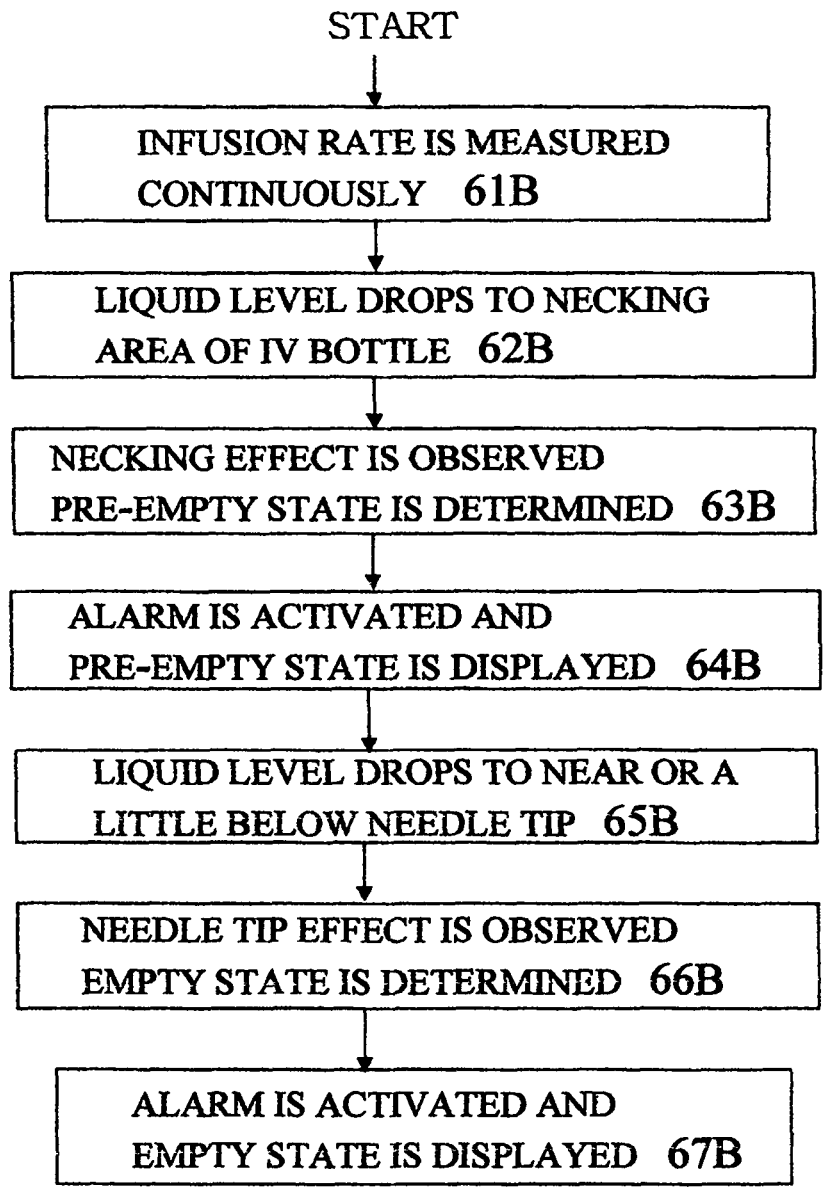
FIG. 6B is the logic flow chart for a methodology based on combined necking and needle tip effect.

FIG. 6B is a logic flow chart to describe the methodology for determining the empty state of the IV bottle 12 based on combined necking and needle tip effect in the present invention. FIG. 6B describes the following 7 steps for this methodology: (a) the infusion rate is measured continuously (61B); (b) liquid level drops to the necking area (62B); (c) the necking effect is observed and then pre-empty state is determined (63B); (d) the alarm is activated and the pre-empty state is displayed (64B); (e) liquid level drops to the needle tip (65B); (f) the needle tip effect is observed and then the empty state is determined (66B); (g) the alarm is activated and the empty state is displayed (67B).

Figure 7:
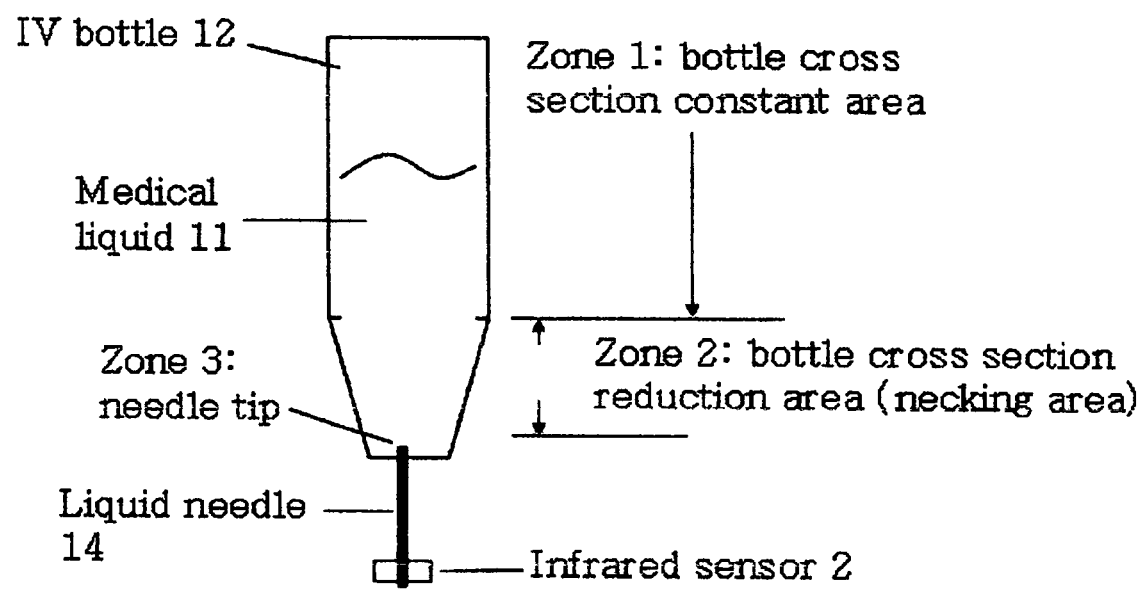
FIG. 7 is the experimental setup to demonstrate necking and needle tip effect.

FIG. 7 is the experimental setup to demonstrate the "necking and needle tip effect." The IV bottle 12 used in the experiment is divided into 3 zones: the bottle cross section constant area (zone 1), the bottle cross section reduction area, i.e., the necking area (zone 2) and the needle tip (zone 3). The medical liquid 11 flows from the IV bottle 12, through the constant cross section (zone 1); then first enters the necking area (zone 2), then enters the tip of liquid needle 14 (zone 3). A pair of infrared sensors 2 are disposed outside the drop chamber 18 (FIG. 1) under the needle tip for more accurate measuring the liquid flow rate (i.e., the infusion rate).

Figure 7A:
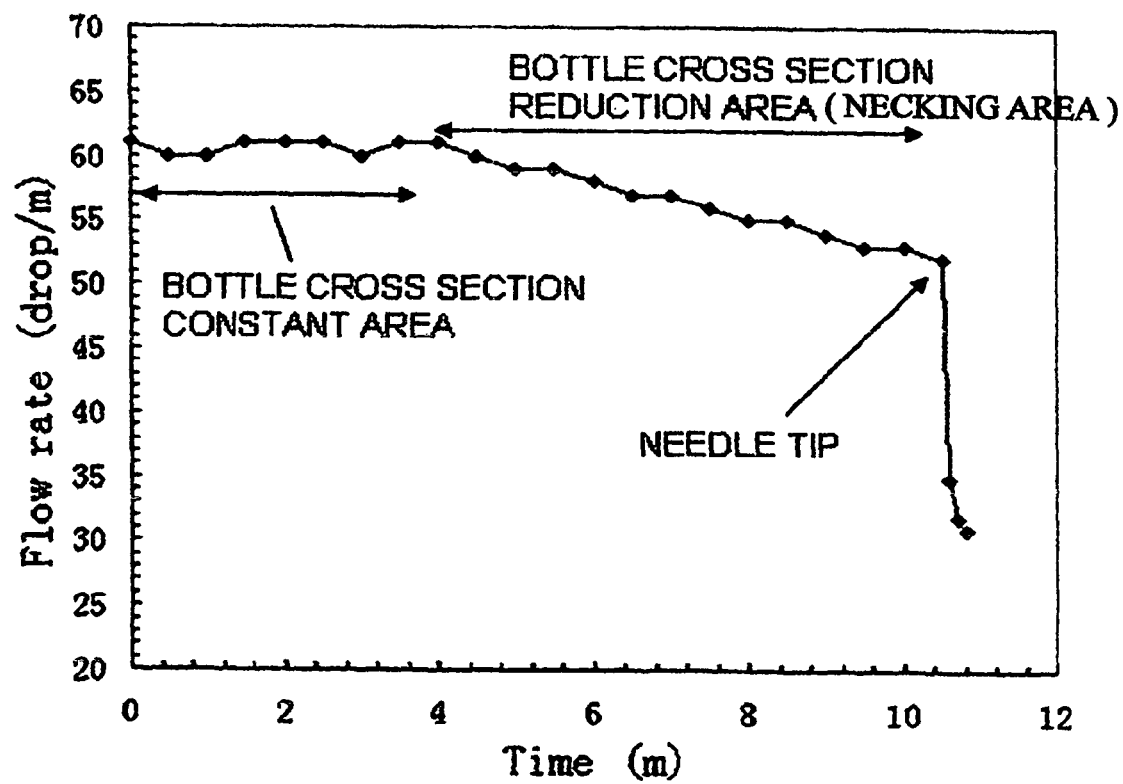
FIG. 7A is the experimental result to verify the necking and needle tip effect.

FIG. 7A shows the experimental results to verify the necking and needle tip effect. The infusion rate (drop per minute) is measured at selected time points in sequence during each zone. It is found that the liquid flow rate is basically constant during the zone 1 (cross section constant area), the liquid flow rate fast and gradually decreases at ~1-2 drops per minute during zone 2 (necking area), and the liquid flow rate sharply drops at the needle tip at ~10 drops per second (zone 3). The reduction rate of the liquid flow rate as the liquid level drops passing the needle tip is at least 300 times faster than that as the liquid level is in the zone 2 (the necking area). The fast and graduate reduction of the infusion rate in zone 2 is called "necking effect." The sharp and abrupt reduction of the infusion rate in zone 3 is called "needle tip effect." As the necking or needle tip effect is observed, we define this moment as the empty state of the IV bottle during infusion. As matter of fact, both effects differ not only in infusion rate reduction but also in its physics.

Figure 7B:
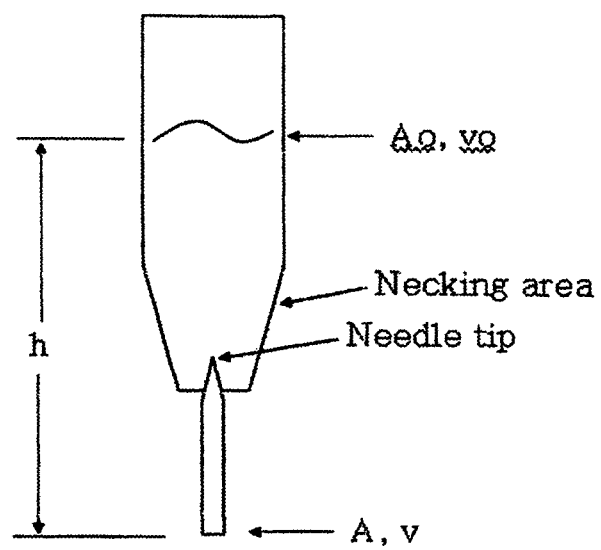
FIG. 7B is the theoretical model to analyze the necking and needle tip effect.

FIG. 7B is the theoretical model to analyze the necking effect and needle tip effect. The Bernoulli equation gives:

$$\Delta p + \rho g h = \frac{\rho}{2}(v^2 - v_o^2). \tag{1}$$

The principal of incompressible flow gives $$A_o v_o = A v, \tag{2}$$

where: $\rho$ density of the medical liquid, g gravitation, h the vertical distance of the liquid in the IV bottle (i.e., the hydraulic head), Ao cross section of the liquid upper surface, A cross section of the liquid lower surface, vo the flow rate at Ao, v the flow rate at A, $\Delta p$ pressure difference between the liquid upper and lower surfaces. Combining Eq. 1 and 2 gives $$\Delta p + \rho g h = \frac{\rho}{2}\left(1 - \frac{A^2}{A_o^2}\right)v^2. \tag{3}$$

Eq. 3 could be expressed in terms of mass velocity $v_m$ (kg/s) as the followings:

$$\Delta p + \rho g h = \frac{1}{2\rho}\left(\frac{1}{A^2} - \frac{1}{A_o^2}\right)v_m^2. \tag{4}$$

The nurse may adjust $\Delta p$ to control the mass flow rate $v_m$ during infusion.

If the liquid level is in zone 1 and zone 2 (see FIG. 7), $$\frac{1}{A_o^2} \ll \frac{1}{A^2},$$ (5)

Eq. 4 becomes $$v_m = A/\sqrt{2\rho(\Delta p + \rho g h)}.$$ (5)

Note that for a given output liquid volume ΔV, the change of hydraulic head Δh is inversely proportional to the cross section area $A_o$, that is $$\Delta V = A_o \Delta h.$$ (6)

In the necking area, $A_o$ reduces fast and gradually, |Δh| increases fast and gradually, that means that h drops fast and gradually, then the mass velocity $v_m$ drops fast and gradually according to Eq. 5. This leads to the case of necking effect in the zone 2. If the liquid level drops to needle tip, $A_0$ is almost zero, $$\frac{1}{A_o^2} \gg \frac{1}{A^2},$$

Eq. 4 becomes $$v_m^2 = -A_0^2 \cdot 2\rho(\Delta p + \rho g h).$$ (7)

In order to have Eq. 7 to be valid, the only solution is:

$A_0$ and $v_m$ are ~zeros. (8)

It leads to the case of needle tip effect in zone 3.

What is claims is:

1. A method for determining empty state of an IV bottle, comprising:
   (a) providing an IV infusion monitoring device for measuring infusion data, said infusion data including weight of remaining medical liquid in said IV bottle, infusion rate, remaining time from completion of IV process, and empty state of said IV bottle, said IV infusion monitoring device comprising:
      (i) a load sensor for measuring gross weight of said IV bottle including said medical liquid and attachments,
      (ii) a signal processor having
         signal amplifier for amplifying said measured weight signal and outputting an amplified weight signal,
         A/D converter for converting said amplified weight signal from analog signal to a group of digital data,
         microprocessor having memory for storing said digital data and having software for statistically analyzing said a group of digital data as well as for calculating said infusion data,
   (b) providing a methodology for determining said empty state of said IV bottle, comprising steps of:
      (i) said infusion rate being measured and calculated continuously,
      (ii) said empty state of said IV bottle being determined if a specific effect is observed, said specific effect being selected from the group consisting of needle tip effect, necking effect, and combined needle tip and necking effect.

2. The method for determining empty state of claim 1 further providing a monitor terminal having
   display means for displaying said infusion data,
   alarm means for giving alarm as said weight of remaining medical liquid in said IV bottle drops to said empty state.

3. The method for determining empty state of claim 1 further providing at least one pair of infrared sensors for detecting said infusion rate.

4. The method for determining empty state of claim 1 further providing a communication network, wherein said infusion data including said empty state being communicated with a server and at least one mobile devices selected from the group consisting of PDA device, laptop computer, palmtop computer, smart phone, smart watches and smart glasses.

5. A method for determining empty state of an IV bottle, comprising:
   (a) providing an IV infusion monitoring device, comprising:
      (i) a load sensor for measuring gross weight of said IV bottle including medical liquid and attachments,
      (ii) a signal processor having
         signal amplifier for amplifying said measured weight signal and outputting an amplified weight signal,
         A/D converter for converting said amplified weight signal from analog signal to a group of digital data,
         microprocessor having memory for storing said digital data as a function of time and having software for encoding said digital data as a function of time,
         data transmitter for transmitting said digital data as a function of time,
   (b) providing a communication network, comprising one server, said monitoring device and said at least one mobile devices, wherein said digital data as a function of time being transmitted to said server, said server having software for analyzing and calculating infusion data, and said infusion data being then transmitted back to said monitoring device and said at least one mobile devices, said infusion data including weight of remaining medical liquid in said IV bottle, infusion rate, remaining time from completion of IV process, and empty state of said IV bottle,
   (c) providing a methodology for determining said empty state of said IV bottle, comprising steps of:
      (i) said infusion rate being measured and calculated continuously,
      (ii) said empty state of said IV bottle being determined if a specific effect is observed, said specific effect being selected from the group consisting of needle tip effect, necking effect, and combined needle tip and necking effect.

6. The method for determining empty state of claim 5 further providing a monitor terminal having
   display means for displaying said infusion data,
   alarm means for giving alarm as said weight of remaining medical liquid in said IV bottle drops to said empty state.

7. The method for determining empty state of claim 5 further providing at least one pair of infrared sensors for detecting said infusion rate.

* * * * *